(12) United States Patent
Tuloup et al.

(10) Patent No.: US 6,384,025 B2
(45) Date of Patent: *May 7, 2002

(54) RETINYL CARBONATE DERIVATIVES, PREPARATION PROCESS AND USES

(75) Inventors: Remy Tuloup, Paris; Maria Dalko, Gif S/Yvette; Gilles Rubinstenn, Paris, all of (FR)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/942,565

(22) Filed: Aug. 31, 2001

Related U.S. Application Data

(63) Continuation of application No. 09/580,833, filed on May 30, 2000, now Pat. No. 6,331,535.

(30) Foreign Application Priority Data

Jun. 1, 1999 (FR) .............................. 99 06872

(51) Int. Cl.[7] .............................. A61K 31/56; C07J 9/00; C07C 69/96
(52) U.S. Cl. ...................... 514/182; 552/544; 536/1.11; 558/260
(58) Field of Search .................. 552/544; 514/182; 536/1.11; 558/260

(56) References Cited

FOREIGN PATENT DOCUMENTS

| JP | 9-185159 | 7/1997 |
|---|---|---|
| WO | WO 95/16659 | 6/1995 |

*Primary Examiner*—Barbara P. Badio
(74) *Attorney, Agent, or Firm*—Oblon, Spivak, McClelland, Maier & Neustadt, P.C.

(57) ABSTRACT

The present invention relates to novel retinol derivatives having the formula (I):

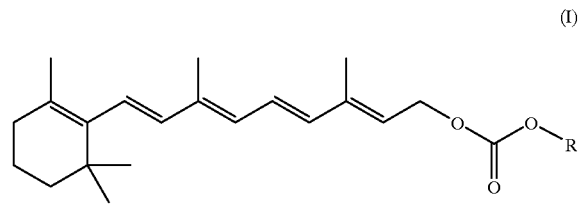

(I)

and to processes for preparing them. The invention also relates to the use of these compounds in or for the preparation of compositions intended for treating conditions of the skin or scalp, for example in preventing or combating acne and/or chronological or actinic ageing of the skin.

22 Claims, No Drawings

RETINYL CARBONATE DERIVATIVES, PREPARATION PROCESS AND USES

This application is a continuation of U.S. application Ser. No. 09/580,833 filed May 30, 2000, now U.S. Pat. No. 6,331,535.

BACKGROUND OF THE INVENTION

1. Field of the Invention

The present invention relates to novel retinyl carbonate derivatives. The invention also relates to the use of these compounds in or for the preparation of compositions intended in particular for preventing or combating acne and/or chronological or actinic ageing of the skin.

2. Discussion of the Background

Retinoid-based cosmetic and/or dermatological compositions have undergone considerable development in recent years. The reason for this is that it has been found that certain compounds of the retinoid family, derived from retinoic acid, are advantageous in skin care, in particular in the treatment of acne and for limiting, or even eliminating altogether, the effects of ageing on the skin such as wrinkles, a weathered appearance, yellowing, loss of elasticity, a ruddy complexion and dryness of the skin, as well as the appearance of blemishes.

These signs of ageing are all the more accentuated when the skin is frequently exposed to sunlight or is particularly sensitive to exposure to UV radiation. Thus, the effects of intrinsic ageing of the skin (age-related) and of light-induced ageing (due to exposure to sunlight) can be cumulative. The manifestations of ageing usually appear at an advanced age; however, their prevention should be undertaken from the start of adult life by suitable care treatments.

Treatment of the skin with compounds of the retinoid family forms part of these preventive or curative care treatments for the signs of ageing.

Among the compounds of the retinoid family, retinol, also known as vitamin A, is most particularly advantageous. The reason for this is that retinol is a natural endogenous constituent of the human body. It is also well tolerated when applied to the skin up to levels that are considerably higher than those for retinoic acid.

However, when it is introduced into a cosmetic composition intended for topical application, retinol degrades rapidly under the effects of light, oxygen, metal ions, oxidizing agents, water or, in particular, under the effect of elevated temperature. There is thus a need for compounds with retinoid-type activity which are more stable than retinol.

WO 95/16659 discloses conjugate compounds obtained from the reaction of retinoids with organic acids or derivatives of these acids. The retinoid, which may be retinol, retinal, retinoic acid or dehydroretinol, is conjugated to the acid derivative, which may be an aldehyde, a ketone, an alcohol, an ester, etc. via an ester, reverse ester, amide or ether bond. Among the very great number of compounds corresponding to this definition, only the ether obtained by reaction of retinol with the hydroxyl function of glycolic acid is described. In particular, no mention is made of retinyl carbonate derivatives.

Moreover, the publications from Svishchuk et al., "Preparation of α-tocopherol (Vitamin E) Ethers", *Farm, Zh.*, 29(6), 36–8 (1974) and from Protopova et al., "Insecticidal Action of 6-hydroxychroman derivatives", *Fiziol. Akt. Veshchestva*, 7, 142–4 (1975) describe, respectively, a tocopheryl retinyl carbonate and an analogous compound in which the side chain of the tocopheryl radical is slightly modified. However, these compounds are not intended for cosmetic use.

SUMMARY OF THE INVENTION

Accordingly, it has now been found that the above-described problems associated with conventional compounds have been solved by the present invention, the first embodiment of which provides a retinol derivative corresponding to formula (I):

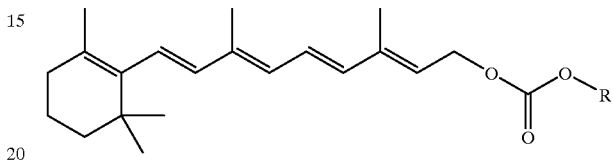

(I)

in which R is selected from the group including:
(a) a linear, cyclic or branched, saturated or unsaturated $C_1$–$C_{18}$ hydrocarbon-based radical, which is unsubstituted or substituted with one or more groups —OH, —OR', —NHCOR, —SH, —SR', —COOH, —CONHR', —COOR', —CN or —CF$_3$, in which R' is a $C_1$–$C_4$ alkyl radical; with a halogen atom; or with:
  (i) one or more saturated or unsaturated, substituted or unsubstituted $C_3$–$C_7$ aliphatic rings, or
  (ii) one or more substituted or unsubstituted aromatic rings, or
  (iii) one or more saturated or unsaturated, substituted or unsubstituted $C_3$–$C_7$ heterocycles, or
  (iv) one or more amino acid or peptide residues;
(b) a radical of cyclopentanephenanthrene structure, which is at least partially hydrogenated and/or substituted,
(c) an aryl radical optionally substituted with one or more groups —OH, —NH$_2$, —SH, —COOH, —CONHR', —NHCOR, —COOR', —OR', —SR', —CN or —CF$_3$, in which R' is a $C_1$–$C_4$ alkyl; with a halogen atom; or with:
  (i) one or more saturated or unsaturated, substituted or unsubstituted $C_3$–$C_7$ aliphatic rings, or
  (ii) one or more substituted or unsubstituted aromatic rings, or
  (iii) one or more saturated or unsaturated, substituted or unsubstituted $C_3$–$C_7$ heterocycles,
wherein substituted chroman groups are excluded;
(d) a group derived from ceramide, sphingosine or sphinganine;
(e) an amino acid or peptide residue bearing a free hydroxyl group; and
(f) a carbohydrate residue.

Another embodiment of the invention provides a composition, which includes:
the retinol derivative described above; and
a physiologically acceptable medium.

Another embodiment of the invention provides a process for preparing the retinol derivative described above, including reacting a chloroformate with retinol.

Another embodiment of the invention provides a process for preparing the retinol derivative described above, including reacting two equivalents of retinol with one equivalent of carbonyldiimidazole.

Another embodiment of the invention provides a method of using the composition described above for the cosmetic treatment of the skin.

Another embodiment of the invention provides a method of using the composition described above for the cosmetic treatment of the scalp.

Another embodiment of the invention provides a method of using retinol derivative described above to prepare a composition intended for the cosmetic treatment of the skin.

Another embodiment of the invention provides a method of using the retinol derivative described above to prepare a composition intended to combat at least one condition selected from the group including acne, chronological aging of the skin, actinic ageing of the skin, and combinations thereof.

Another embodiment of the invention provides a method of using the retinol derivative described above to prepare a composition intended to combat at least one condition selected from the group including the greasy appearance of the hair and hair loss.

Another embodiment of the invention provides a method of combating or treating at least one condition selected from the group including acne, chronological aging of the skin, actinic ageing of the skin, greasy appearance of the hair, hair loss, and combinations thereof, that includes applying to the skin or scalp the retinol derivative described above.

Another embodiment of the invention provides a method of combating or treating at least one condition selected from the group including acne, chronological aging of the skin, actinic ageing of the skin, greasy appearance of the hair, hair loss, and combinations thereof, that includes applying to the skin or scalp the composition described above.

DETAILED DESCRIPTION OF THE INVENTION

Various other objects, features and attendant advantages of the present invention will be more fully appreciated as the same becomes better understood from the following detailed description of the preferred embodiments of the invention.

Preferably, the derivatives of formula (I) can be defined as the products of condensation of retinol with other compounds bearing an alcohol function, via a carbonate bond.

Preferable linear hydrocarbon-based radicals containing from 1 to 18 carbon atoms include methyl, ethyl, propyl, butyl, hexyl, octyl, decyl, dodecyl, hexadecyl and octadecyl radicals.

Preferable branched hydrocarbon-based radicals containing from 1 to 18 carbon atoms include 2-ethylhexyl, 2-butyloctyl and 2-hexyldecyl radicals.

The unsaturated hydrocarbon-based radicals are preferably radicals containing one or more ethylenic unsaturations, such as 2-nonyl-2-butenyl, geranyl, 2,4-cyclohexadienyl and allyl radicals.

Preferable cyclic hydrocarbon-based radicals containing from 1 to 18 carbon atoms and $C_3$–$C_7$ aliphatic rings include cyclobutyl, cyclohexyl and tert-butylcyclohexyl radicals.

The linear, branched or cyclic $C_1$–$C_{18}$ hydrocarbon-based radicals substituted with hydroxyl groups preferably include polyol residues, such as 2,3-dihydroxypropyl, 2,3,4-trihydroxybutyl, 2,3,4,5-tetrahydroxypentyl and 2,3,4,5,6-penta-hydroxyhexyl radicals or a pentaerythritol residue, and more preferably sugar residues derived, for example, from glucose, galactose or mannose, or alternatively from glucuronic acid.

The linear, branched or cyclic $C_1$–$C_{18}$ hydrocarbon-based radicals substituted with —COOH groups preferably include α-hydroxy acid residues, optionally in lactonized form, or β-hydroxy acid residues, such as a malic acid, tartaric acid, glycolic acid, lactic acid, ascorbic acid or salicylic acid residue or derivatives thereof.

The radicals of cyclopentanephenanthrene structure which are at least partially hydrogenated and/or substituted preferably include steryl and oxysteryl radicals, and in particular the cholesteryl radical; sapogenin residues, and in particular diosgenin, hecogenin and smilagenin residues; and a dehydro-epi-androsterone residue.

The term "$C_3$–$C_7$ heterocycle" preferably means pyridine, furan, thiophene and pyrrole.

The terms "aryl radical" and "aromatic ring" preferably mean a phenyl radical optionally substituted with at least one halogen atom, one hydroxyl or one nitro function.

The term "amino acid residue" preferably means a residue derived from lysine, glycine, aspartic acid or cysteine, and the term "peptide residue" more preferably means a dipeptide or tripeptide residue resulting from the combination of amino acids. Preferable amino acid residues bearing a free hydroxyl group include serine and tyrosine.

The term "carbohydrate residue" prefeably means a residue derived from glucose, galactose, mannose, lactose, melibiose or sorbitol, or alternatively from glucuronic acid.

Preferably, the retinol derivative according to the invention is a retinyl cholesteryl carbonate, which corresponds to the general formula (I) above in which R is a cholesteryl radical.

According to another preferred embodiment of the invention, the retinol derivative of formula (I) is retinyl carbonate, i.e. R represents a retinyl radical.

The invention also extends its scope to a process for preparing the abovementioned retinyl carbonate derivatives.

According to a first synthetic route, which makes it possible to prepare the set of compounds of formula (I), the process according to the invention preferably includes the step of reacting a chloroformate with retinol. The reaction is preferably carried out in anhydrous medium and under inert atmosphere, so as to protect the retinol against the oxidation which it has a tendency to undergo in aqueous medium and/or on contact with atmospheric oxygen.

The reaction carried out is illustrated in Figure (II):

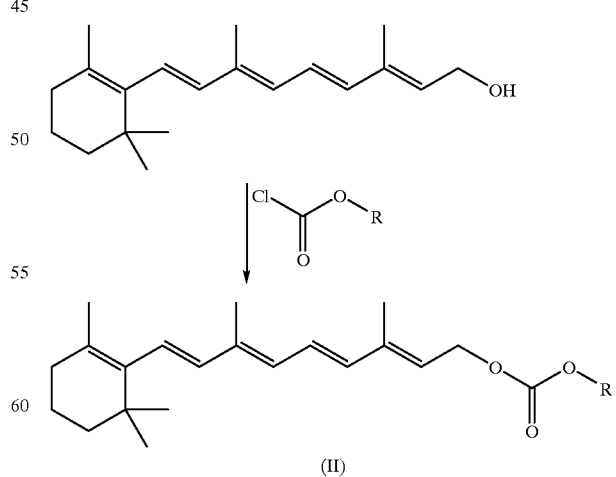

(II)

According to a second synthetic route, which can be used when the retinyl carbonate derivative is retinyl carbonate, the process according to the invention preferably includes the step of reacting two equivalents of retinol with one equivalent of carbonyldiimidazole. As previously, the reaction is preferably carried out in anhydrous medium and under an inert atmosphere.

The reaction scheme is illustrated in Figure (III):

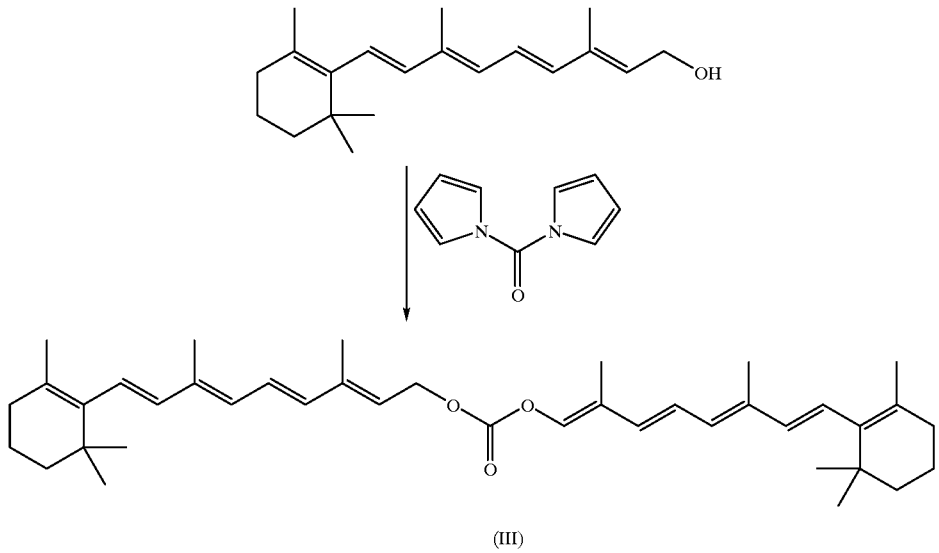

(III)

The invention also preferably relates to a composition including, in a physiologically acceptable medium, at least one retinyl carbonate derivative as defined above. The expression "physiologically acceptable" preferably means a medium which is compatible with the skin and its superficial body growths (nails, hairs) and/or with head hair.

The physiologically acceptable medium in which the compounds according to the invention may be used, as well as its constituents, their amount, the pharmaceutical form of the composition and the method for preparing it, can be chosen by a person skilled in the art on the basis of his or her general knowledge as a function of the type of composition desired.

The composition according to the invention can be in any pharmaceutical form normally used for topical application to the skin, in particular in the form of an aqueous, aqueous-alcoholic or oily solution, an oil-in-water or water-in-oil or multiple emulsion, a silicone emulsion, a microemulsion or nanoemulsion, an aqueous or oily gel, a liquid, pasty or solid anhydrous product, a dispersion of oil in an aqueous phase in the presence of spherules, these spherules possibly being polymer nanoparticles such as nanospheres and nanocapsules or, better still, lipid vesicles of ionic and/or nonionic type.

This composition can be more or less fluid and can have the appearance of a white or coloured cream, an ointment, a milk, a lotion, a serum, a paste, a mousse or a gel. It can optionally be applied to the skin in the form of an aerosol. It can also be in solid form, and for example in the form of a stick. It can be used as a care product and/or as a make-up product for the skin, or as a hair product, for example as a shampoo or conditioner.

In a known manner, the composition of the invention can also contain adjuvants that are common in cosmetics and dermatology, such as hydrophilic or lipophilic gelling agents, hydrophilic or lipophilic active agents, preserving agents, antioxidants, solvents, fragrances, fillers, screening agents, pigments, odour absorbers and dyestuffs. The amounts of these various adjuvants are those conventionally used in the fields under consideration, and for example from 0.01 to 20% relative to the total weight of the composition. Depending on their nature, these adjuvants can be introduced into the fatty phase, into the aqueous phase, into the lipid vesicles and/or into the nanoparticles. These adjuvants and their concentrations should be such that they do not harm the advantageous properties of the retinol derivative or retinyl carbonate derivative according to the invention.

When the composition according to the invention is an emulsion, the proportion of the fatty phase can range from 5 to 80% by weight, and preferably from 5 to 50% by weight, relative to the total weight of the composition. The fatty substances, the emulsifiers and the co-emulsifiers used in the composition in emulsion form are chosen from those conventionally used in the field under consideration. The emulsifier and the co-emulsifier are preferably present in the composition in a proportion ranging from 0.3 to 30% by weight, and preferably from 0.5 to 20% by weight, relative to the total weight of the composition.

As fatty substances which can be used in the invention, oils and in particular mineral oils (liquid petroleum jelly), oils of plant origin (avocado oil, soybean oil), oils of animal origin (lanolin), synthetic oils (perhydrosqualene), silicone oils (cyclomethicone) and fluoro oils (perfluoropolyethers) can be used. Fatty alcohols such as cetyl alcohol, fatty acids, waxes and gums and in particular silicone gums, can also be used as fatty substances.

As emulsifiers and co-emulsifiers which can be used in the invention, mention may be made for example of fatty acid esters of polyethylene glycol, such as PEG-100 stearate; fatty acid esters of glycerol, such as glyceryl stearate; fatty acid esters of sorbitan, which are optionally oxyalkylenated; and mixtures thereof.

Hydrophilic gelling agents which may be mentioned in particular are carboxyvinyl polymers (carbomer), acrylic copolymers such as acrylate/alkylacrylate copolymers, polyacrylamides, polysaccharides, natural gums and clays, and lipophilic gelling agents which may be mentioned are modified clays such as bentones, metal salts of fatty acids and hydrophobic silica.

Active agents which can be used in particular are depigmenting agents, emollients, moisturizers, anti-seborrhoeic agents, anti-acne agents, agents for promoting the regrowth of the hair, keratolytic and/or desquamating agents, anti-irritant agents or calmants and mixtures thereof. Advantageously, in the composition according to the invention, the retinyl carbonate derivatives defined above will be used in combination with other compounds of retinoid-type activity, with free-radical scavengers or with α-hydroxy or α-keto acids or derivatives thereof. The expression "free-radical scavenger" preferably means, for example, α-tocopherol, superoxide dismutase, ubiquinol or certain metal-chelating agents. The expression "α-hydroxy or α-keto acids or derivatives thereof" preferably means, for example, lactic acid, malic acid, citric acid, glycolic acid, mandelic acid, tartaric acid or glyceric acid or their salts, amides or esters.

In the event of incompatibility, the active agents mentioned above can be incorporated into spherules, in particular ionic or nonionic vesicles and/or nanoparticles (nanocapsules and/or nanospheres), so as to isolate them from each other in the composition.

The composition according to the invention is particularly suitable in the applications of body and hair hygiene and especially for the care of squamous or acne-prone skin, to combat the greasy appearance of the skin or the hair, to combat hair loss, in protecting against the harmful aspects of sunlight or to prevent and/or combat actinic or chronological ageing.

A preferred embodiment of the present invention is thus also the use of the composition mentioned above for the cosmetic treatment of the skin, in particular against acne and/or chronological or actinic ageing. The invention also relates to the use of this composition for the cosmetic treatment of the scalp, in particular to combat the greasy appearance of the hair and hair loss.

A preferred embodiment of the present invention is also the use of the retinol derivatives defined above to prepare a composition intended to combat acne and/or chronological or actinic ageing of the skin. The invention also relates to the use of these retinol derivatives to prepare a composition intended to combat the greasy appearance of the hair and hair loss.

Another preferred embodiment of the invention relates to the use of the retinol derivatives and compositions containing them for preventing or combating acne and/or chronological or actinic ageing of the skin.

The composition according to the invention preferably includes an effective amount of at least one retinol derivative as defined above, which is sufficient to obtain the desired effect, and a physiologically acceptable medium. The composition according to the invention thus preferably includes, for example, from 0.001 to 20% by weight, more preferably from 0.01 to 10% by weight and most preferably from 0.1 to 5% by weight, of retinol derivative relative to the total weight of the composition. Most preferably, the retinol derivative is a retinyl carbonate derivative.

EXAMPLES

Having generally described this invention, a further understanding can be obtained by reference to certain specific examples which are provided herein for purposes of illustration only and are not intended to be limiting unless otherwise specified.

Example 1

Retinyl Cholesteryl Carbonate a) Preparation Process

One molar equivalent of retinol and one molar equivalent of cholesteryl chloroformate are dissolved in anhydrous dichloromethane, under an inert atmosphere, at room temperature. Pyridine (3.5 molar equivalents) is added and the reaction medium is stirred for 20 minutes.

After dilution with dichloromethane, washing with water, concentration and co-evaporation of the pyridine with toluene, the final product of formula (IV) below is recrystallized from acetone.

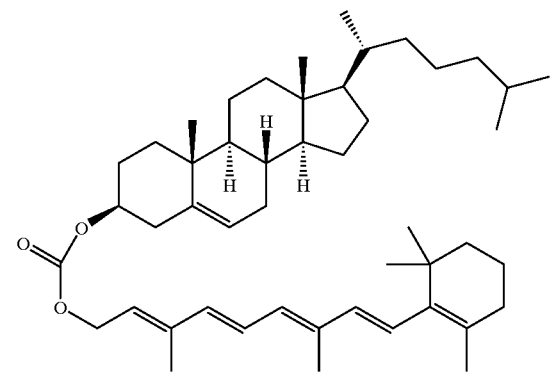

(IV)

b) NMR characterization $C^{13}$ NMR (100 MHz in $CDCl_3$) d (in ppm): 154.82, 139.57, 139.42, 137.83, 137.57, 136.7, 135.72, 129.9, 125.35, 127.06, 126.02, 123.84, 122.89, 77.89, 64.26, 56.72, 56.18, 50.5, 42.34, 39.75, 39.66, 39.54, 38.07, 36.89, 36.56, 36.20, 35.78, 34.26, 33.06, 31.91, 31.87, 28.95 (2 C), 28.21, 28.00, 27.73, 24.28, 23.84, 22.79, 22.54, 21.69, 21.06, 19.27, 19.25, 18.72, 12.78, 12.72, 11.85.

$^1H$ NMR (400 MHz in $CDCl_3$) d (in ppm): 6.64 (dd, 11.3 Hz, 15.2 Hz, 1H), 6.26 (d, 15.2 Hz, 1H), 6.18 (d, 16.1 Hz, 1H), 6.10 (d, 16.3 Hz, 1H), 6.09 (d, 11.2 Hz, 1H), 5.40–5.38 (m, 1H), 4.77 (d, 7.25, 2H), 4.51–4.44 (m, 1H), 2.40–0.85 (m, 62H), 09.67 (s, 3H).

Example 2

Retinyl Carbonate a) Preparation Process

Two equivalents of retinol and one molar equivalent of carbonyldiimidazole are dissolved in anhydrous tetrahydrofuran, under an inert atmosphere, at room temperature. The reaction medium is stirred for two hours, with the tetrahydrofuran maintained at reflux.

After concentrating, taking the residue up in ether, washing the ether phase with water and concentrating, the product of formula (V) below is obtained in a purity of greater than 90% (only traces of retinol are detected by $^1H$ NMR).

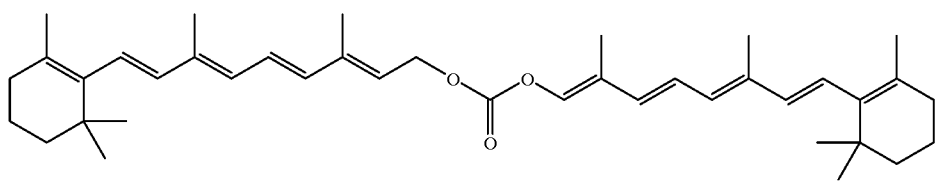

(V)

b) NMR characterization $C^{13}$ NMR (50 MHz in $CDCl_3$) d (in ppm): 155.2, 139.9, 137.9, 137.7, 136.9, 135.8, 130.0, 129.5, 127.2, 126.6, 123.8, 64.72, 37.3, 34.3, 33.2, 29.1, 21.9, 19.4, 12.9.

$_1H$ NMR (200 MHz in $CDCl_3$) d (in ppm): 6.59 (dd. 11.2 Hz, 15.0 Hz, 2H), 6.20 (d, 15.0 Hz, 2H), 6.10–5.97 (m, 4H), 5.60–5.52 (m, 2H), 4.72 (d, 7.26 Hz, 4H), 1.97–1.36 (m, 32H), 0.95 (s, 12H).

Example 3

This example illustrates various cosmetic formulations based on the retinol derivatives according to the invention.

Anti-ageing Cream in the Form of a W/O Emulsion

| | |
|---|---|
| Oxyethylenated polymethylcetyl dimethyl methylsiloxane | 1.5% |
| Polyglyceryl isostearate | 0.5% |
| Isohexadecane | 12.7% |
| Compound of Example 1 | 0.2% |
| Butyl hydroxytoluene | 0.1% |
| Mixture of acetylated ethylene glycol stearate and glyceryl tristearate, sold by the company Guardian under the name Unitwix | 1% |
| Preserving agents | 0.4% |
| Apricot kernel oil | 5% |
| Glycerol | 5% |
| Magnesium sulphate | 0.7% |
| Disodium salt of EDTA | 0.1% |
| Imidazolinylurea | 0.3% |
| Water qs | 100% |

Anti-ageing Fluid in the Form of an O/W Emulsion

| | |
|---|---|
| Mixture of glyceryl monostearate and poly-ethylene glycol stearate (100 EO) | 2.1% |
| Cetyl alcohol | 2.6% |
| Hydrogenated isoparaffin | 14.8% |
| Preserving agents | 0.4% |
| Compound of Example 1 | 0.1% |
| Butyl hydroxytoluene | 0.1% |
| Oxyethylenated sorbitan monostearate (20 EO) | 0.9% |
| Glycerol | 3% |
| Xanthan gum | 0.1% |
| Carbomer | 0.4% |
| Imidazolinylurea | 0.3% |
| Triethanolamine | 0.3% |
| Water qs | 100% |

Anti-ageing Fluid in the Form of an O/W Emulsion

| | |
|---|---|
| Sorbitan tristearate | 0.9% |
| Polyethylene glycol stearate (40 EO) | 2% |
| Cetyl alcohol | 4% |
| Glyceryl stearate | 3% |
| Compound of Example 2 | 0.4% |
| Butyl hydroxytoluene | 0.1% |
| Hydrogenated isoparaffin | 1.8% |
| Preserving agents | 0.40% |
| Cyclopentasiloxane | 10% |
| Imidazolidinylurea | 0.3% |
| Water qs | 100% |

Obviously, numerous modifications and variations of the present invention are possible in light of the above teachings. It is therefore to be understood that within the scope of the appended claims, the invention may be practiced otherwise than as specifically described herein.

This application is based on French Patent Application FR 9906872, filed Jun. 1, 1999, and incorporated herein by reference in its entirety.

What is claimed is:

1. A retinol derivative of formula (I):

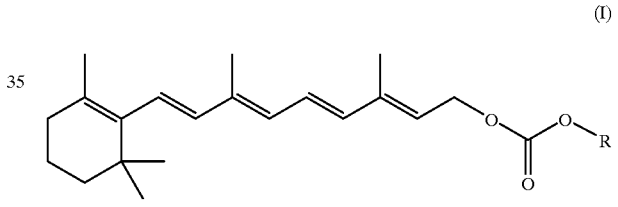

(I)

wherein R is selected from the group consisting of:
(a) an unsubstituted cyclic, saturated or unsaturated, $C_1$–$C_{18}$ hydrocarbon-based radical, an unsubstituted linear or branched, saturated or unsaturated, $C_{12}$–$C_{18}$ hydrocarbon-based radical, or a substituted linear, cyclic or branched, saturated or unsaturated $C_1$–$C_{18}$ hydrocarbon-based radical, which is substituted with one or more groups —OH, —OR', —NHCOR, —SH, —SR', —COOH, —CONHR', —COOR', —CN or —$CF_3$, in which R' is a $C_1$–$C_4$ alkyl radical; with a halogen atom; or with:
 (i) one or more saturated or unsaturated, substituted or unsubstituted $C_3$–$C_7$ aliphatic rings, or
 (ii) one or more substituted or unsubstituted aromatic rings, or
 (iii) one or more saturated or unsaturated, substituted or unsubstituted $C_3$–$C_7$ heterocycles, or
 (iv) one or more amino acid or peptide residues,
(b) a radical of cyclopentanephenanthrene structure, which is at least partially hydrogenated and/or substituted,
(c) an aryl radical optionally substituted with one or more groups —OH, —$NH_2$, —SH, —COOH, —CONHR', —NHCOR, —COOR', —OR', —SR', —CN or —$CF_3$, in which R' is a $C_1$–$C_4$ alkyl; with a halogen atom; or with:

(i) one or more saturated or unsaturated, substituted or unsubstituted $C_3$–$C_7$ aliphatic rings, or (ii) one or more substituted or unsubstituted aromatic rings, or (iii) one or more saturated or unsaturated, substituted or unsubstituted $C_3$–$C_7$ heterocycles, wherein substituted chroman groups are excluded;

(d) a group derived from ceramide, sphingosine or sphinganine;

(e) an amino acid or peptide residue bearing a free hydroxyl group; and (f) a carbohydrate residue.

2. The retinol derivative of claim 1, wherein R is a carbohydrate residue.

3. The retinol derivative of claim 2, wherein the carbohydrate residue is glucose, galactose, mannose, lactose, melibiose, sorbitol or glucuronic acid.

4. The retinol derivative of claim 3, wherein the carbohydrate residue is glucose.

5. The retinol derivative of claim 3, wherein the carbohydrate residue is lactose.

6. The retinol derivative of claim 3, wherein the carbohydrate residue is melibiose.

7. The retinol derivative of claim 3, wherein the carbohydrate residue is galactose.

8. The retinol derivative of claim 3, wherein the carbohydrate residue is mannose.

9. The retinol derivative of claim 3, wherein the carbohydrate residue is sorbitol.

10. The retinol derivative of claim 3, wherein the carbohydrate residue is glucuronic acid.

11. A composition comprising the retinol derivative of claim 2 and a physiologically acceptable medium.

12. A composition comprising the retinol derivative of claim 3 and a physiologically acceptable medium.

13. The composition according to claim 11, further comprising at least one active agent selected from the group consisting of depigmenting agents, emollients, moisturizers, anti-seborrhoeic agents, anti-acne agents, agents for promotng regrowth of the hair, keratolytic and/or desquamating agents, anti-irritant agents or calmants and mixtures thereof.

14. The composition according to claim 12, further comprising at least one active agent selected from the group consisting of depigmenting agents, emollients, moisturizers, anti-seborrhoeic agents, anti-acne agents, agents for promoting regrowth of the hair, keratolytic and/or desquamating agents, anti-irritant agents or calmants and mixtures thereof.

15. The composition according to claim 11, further comprising a free radical scavenger, an α-hydroxy acid or an α-keto acid.

16. The composition according to claim 12, further comprising a free radical scavenger, an α-hydroxy acid or an α-keto acid.

17. A method of combating or treating at least one condition selected from the group consisting of acne, chronological aging of the skin, actinic aging of the skin, greasy appearance of the hair, hair loss, and a combination thereof, comprising applying to the skin or scalp the retinol derivative of claim 2.

18. A method of combating or treating at least one condition selected from the group consisting of acne, chronological aging of the skin, actinic aging of the skin, greasy appearance of the hair, hair loss, and a combination thereof, comprising applying to the skin or scalp the retinol derivative of claim 3.

19. A method of combating or treating acne comprising applying to the skin or scalp the retinol derivative of claim 2.

20. A method of combating or treating acne comprising applying to the skin or scalp the retinol derivative of claim 3.

21. A method of combating or treating chronological aging of the skin or actinic aging of the skin comprising applying to the skin or scalp the retinol derivative of claim 2.

22. A method of combating or treating chronological aging of the skin or actinic aging of the skin comprising applying to the skin or scalp the retinol derivative of claim 3.

* * * * *

UNITED STATES PATENT AND TRADEMARK OFFICE
CERTIFICATE OF CORRECTION

PATENT NO.   : 6,384,025 B2
DATED        : May 7, 2002
INVENTOR(S)  : Remy Tuloup et al.

It is certified that error appears in the above-identified patent and that said Letters Patent is hereby corrected as shown below:

<u>Column 11,</u>
Line 41, "promotng" should read -- "promoting" --.

Signed and Sealed this

Ninth Day of July, 2002

*Attest:*

*Attesting Officer*

JAMES E. ROGAN
*Director of the United States Patent and Trademark Office*